United States Patent
Takai et al.

(10) Patent No.: US 7,265,261 B2
(45) Date of Patent: Sep. 4, 2007

(54) NON-HUMAN ANIMAL MODEL OF SYSTEMIC LUPUS ERYTHEMATOSUS

(75) Inventors: Toshiyuki Takai, Sendai (JP); Akira Nakamura, Sendai (JP); Kaori Yajima, Sendai (JP)

(73) Assignee: Japan Science and Technology Agency, Kawaguchi-Shi (JP)

( * ) Notice: Subject to any disclaimer, the term of this patent is extended or adjusted under 35 U.S.C. 154(b) by 0 days.

(21) Appl. No.: 10/493,967

(22) PCT Filed: Oct. 25, 2002

(86) PCT No.: PCT/JP02/11106

§ 371 (c)(1),
(2), (4) Date: Aug. 31, 2004

(87) PCT Pub. No.: WO03/037080

PCT Pub. Date: May 8, 2003

(65) Prior Publication Data

US 2005/0066378 A1    Mar. 24, 2005

(30) Foreign Application Priority Data

Oct. 29, 2001  (JP) .............................. 2001-331621

(51) Int. Cl.
*A01K 67/00*    (2006.01)
(52) U.S. Cl. ........................................ 800/18
(58) Field of Classification Search ...................... None
See application file for complete search history.

(56) References Cited

FOREIGN PATENT DOCUMENTS

JP    2001-178308 A    7/2001

WO    1995/028959 A1    11/1995

OTHER PUBLICATIONS

Paisansinsup et al. J. Immuno. 167(7):4083-90, Oct. 1, 2001.*
Seery, JP et al. J immuno 167:2452-2455, 2001.*
Paisansinsup, T et al. J Immuno 167:4083-4090.*
Wall, RJ. Theriogenology 45:57-68, 1996.*
Cameron, ER. Molec Biotech 7:253-265, 1997.*
Sigmund, CD. Art. Thromb. Vasc. Biol. 20:1425-1429, 2000.*
Niemann, H. Transgenic Res. 7:73-75, 1998.*
Kappel, C.A. et al. Current Opinion Biotech 3:548-553, 1992.*

(Continued)

*Primary Examiner*—Anne-Marie Falk
*Assistant Examiner*—Marcia S. Noble
(74) *Attorney, Agent, or Firm*—Foley and Lardner LLP

(57) ABSTRACT

The present invention is to provide a non-human animal model of systemic lupus erythematosus wherein generation of anti-double stranded DNA antibody and anti-single stranded antibody is induced, and that is made to spontaneously develop glomerulonephritis and arthritis, and a screening method for a therapeutic agent for systemic lupus erythematosus wherein the non-human animal model is used. FcγRIIB deficient mouse that is not made to spontaneously develop autoimmune pathology although its autoantibody response is enhanced is backcrossed into C57BL/6J (B6) mouse for 12 generations to generate FcγRIIB deficient B6 mouse, the FcγRIIB deficient B6 male mouse is intercrossed with lpr/B6 female mouse, and thus obtained FcγRIIB$^{+/-}$/lpr$^{+/-}$ mice were further crossed to generate a mouse model of systemic lupus erythematosus.

1 Claim, 8 Drawing Sheets

OTHER PUBLICATIONS

Mullins, LJ and JJ Mullins. J Clin Invest 98(11) Supplement; S37-S40, 1996.*

Mullins, JJ and LJ Mullins. Hypertension 22:630-633, 1993.*

Houdebine, LM. J Biotech 34:269-287, 1994.*

Maria Marino et al., "Prevention of systemic lupus erythematosus in MRL/*lpr* mice by administration of an immunoglobulin-binding peptide", *Nature Biotechnology*, vol. 18, pp. 735-739, Jul. 2000.

Toshiyuki Takai et al., "Augmented humoral and anaphylactic responses in FCγRII-deficient mice", *Nature*, vol. 379, pp. 346-349, Jan. 25, 1996.

K. Bernstein et al., "Detection of glomerular-binding immune elements in murine lupus using a tissue-based ELISA", *Clin. Exp. Immunol.*, vol. 91, pp. 449-455, 1993.

Belen de Andrés et al., "FcγRII (CD32) Is Linked to Apoptotic Pathways in Murine Ganulocyte Precursors and Mature Eosinophils", *Blood*, vol. 90, No. 3, pp. 1267-1274, Aug. 1, 1997.

Gabriella Sármay et al., "Cooperation between SHP-2, phosphatidyl inositol 3-kinase and phosphoinositol 5-phosphatase in the FCγRII*b* mediated B cell regulation", *Immunology Letters*, vol. 68, pp. 25-34, 1999.

Wakeland, Edward et al., "Delineating the Genetic Basis of Systemic Lupus Erythematosus", Immunity, vol. 15, Sep. 23, 2001, pp. 397-408.

Bollard, Silvia et al., "Spontaneous Autoimmune Disease in FcγRIIB-Deficient Mice Results from Strain-Specific Epistasis", Laboratory of Molecular Genetics and Immunology, vol. 13, Aug. 2000, pp. 277-285.

Morel, Laurence, et al., "Genetic reconstitution of systemic lupus erythematorus immunopathology with polycongenic murine strains", Proc Natl Acad Sci USA, vol. 97, Jun. 6, 2000, pp. 6670-6675.

Lindqvist, A. K. B. et al. "The Genetics of Systemic Lupus Erythematosus", Scand J. Immunol, vol. 50, Dec. 1999, pp. 562-571.

Yajima, Kaori et al., "FcγRIIB deficiency with Fas mutation is sufficient for the development of sytemic autoimmune disease", Eur J. Immunol, vol. 33, Mar. 2003-Apr. 2003, pp. 1020-1029.

Bolland, Silvia et al., "Genetic Modifiers of Systemic Lupus Erythematosus in FcγRIIB (-/-) Mice", J. Exp. Med., vol. 9, May 6, 2002, pp. 1167-1174.

Jiang, Yi et al., "Genetically determined aberrant down-regulation of FcγRIIB1 in germinal center B cells associated with hyper-IgG and IgG autoantibodies in murine systemic lupus erythematosus", International Immunology, vol. 11, Oct. 1999, pp. 1685-1691.

Pritchard, Nicholas et al., "Autoimmune-prone mice share a promoter haplotype associated with reduced expression and function of the Fc receptor FcγRll", Current Biology, vol. 10, Feb. 11, 2000, pp. 227-230.

* cited by examiner

NON-HUMAN ANIMAL MODEL OF SYSTEMIC LUPUS ERYTHEMATOSUS

TECHNICAL FIELD

The present invention relates to a non-human animal model that develops systemic lupus erythematosus, which is systemic autoimmune disease, and a screening method and the like of a therapeutic agent for systemic lupus erythematosus using said non-human animal model of systemic lupus erythematosus.

BACKGROUND ART

Living bodies show allergic reaction not only to foreign substances of the outer world, but also to their own components, resulting in the development of autoimmune disorders. Such autoimmune disorders are systemic diseases which are divided into organ-specific autoimmune diseases such as pernicious anemia, Goodpasture's syndrome, myasthenia gravis, insulin-resistant diabetes, atrophic nephritis, multiple sclerosis and the like, and organ-nonspecific autoimmune diseases such as rheumatoid arthritis, systemic lupus erythematosus, polymyositis and the like. Various autoantibodies and autoantigen-reactive lymphocytes are present in such autoimmune disease, and it has been an important issue how they are actually related to tissue disorder. The above-mentioned systemic lupus erythematosus (SLE) is a typical systemic autoimmune disease that shows immune abnormality such as expression of various autoimmune and the like, and expresses multiple organ failures. Genetic factors and dysfunction of T cells and B cells that cause generation of various autoantibodies including mainly anti-double stranded DNA antibody (anti-ds DNA antibody) have been pointed out as the cause of the disease. Actual clinical symptoms are various, being systemic such as mucocutaneous symptoms, arthritis, pleurisy/pericarditis, neuropsychiatric disorder and the like, and particularly, glomerulonephritis is an important lesion which determines life prognosis.

Conventionally, MRL/lpr mice have been known as typical mouse model of systemic lupus erythematosus (Murphy E D, Roth J B: Autoimmunity and lymphoproliferation: Induction by mutant gene lpr, and acceleration by a male-associated factor in strain BXSB mouse. Genetic Control of Autoimmune Disease (eds. Rose N, Bigazzi P, Warner N), Elsevier North Holland, N.Y., 1978, p 207-221), the MRL/lpr mice are inbred mice by crossing AKR/J, C57BL/6J, C3H/Di, and LG/J, that develops spontaneously arthritis and glomerulonephritis. It has been acknowledged that Lpr gene is an autosomal recessive mutant gene causing proliferation of lymphocytes, which is a mutant of Fas antigen gene inducing apoptosis, and that MRL/lpr mice are deficient type of Fas antigen gene (Watanabe-Fukunaga R, Brannan C I, Copeland N G, Jelkins N A, Nagata S: Lymphoproliferation disorder in mice explained by defects in Fas antigen that mediates apoptosis. Nature 356:314-317, 1992; Takahashi, T., Tanaka, M., Brannan, C. I., Jenkins, N. A., Copeland, N. G., Suda, T., and Nagata, S. (1994). Generalized lymphoproliferative disease in mice, caused by a point mutation in the Fas ligand. Cell 76, 969-976). Although abnormal proliferation of T cells and B cells/overgeneration of immunoglobulin and their detailed mechanism are unknown, it has been reported that generation of various autoantibodies (anti-DNA antibody, anti-Sm antibody and the like) can be induced in the same manner as human diseases (Izui S, Eisenberg R A: Circulating anti-DNA-rheumatoid factor complex in MRL/l mice. Clin Immunol Immunopathological 15:436-551, 1980; Gyotoku Y, Abdelmoula M, Spertini F, Izui S, Lambert P-H: Crioglobulinemia induced by monoclonal immunoglobulin G rheumatoid factors derived from autoimmune MRL/Mpj-lpr/lpr mice. J Immunol 138:3785-3792, 1987). Further, MRL/lpr mice are mice wherein different haplotypes are mixed as mentioned above, and it is known that if they are backcrossed into mice of a strain that develops spontaneously autoimmune abnormality (C3H/HeJ, C57BL/6, AKR), diseases such as arthritis and nephritis are not developed, although autoantibody generation can be observed (Theofilopoulos, A. N., and F. J. Dixon: Murine models of systemic lupus erythematosus. Adv. Immunol. 37:269-390, 1985). Therefore their genetic background is considered to be closely related to the autoimmune pathology of MRL/lpr. On the other hand, Japanese Laid-Open Patent Application No. 9-172908 discloses non-human transgenic vertebrate of systemic lupus erythematosus wherein exogenous genetic structure including IL-1 α gene is incorporated.

The object of the present invention is to provide a non-human animal model of systemic lupus erythematosus wherein generation of anti-double stranded DNA antibody and anti-single stranded DNA antibody is induced, and that develops spontaneously arthritis and glomerulonephritis; and a screening method for a therapeutic agent for systemic lupus erythematosus using said non-human animal model of systemic lupus erythematosus.

The present inventors made a keen study to solve the above problem, and they backcrossed for 12 generations FcγRIIB deficient mouse that does not develop spontaneously autoimmune pathology although its various antibody responses are enhanced, wherein genetic function of FcγRIIB which is inhibitory FcR is deficient on its chromosome, into C57BL/6J (B6) mouse which is a haplotype H-2b to generate FcγRIIB deficient B6 mouse, intercrossed the FcγRIIB deficient B6 male mouse with an Lpr/B6 female mouse to generate FcγRIIB$^{+/-}$/lpr$^{+/-}$ mouse wherein the both genes are heterozygous; they further crossed the FcγRIIB$^{+/-}$/lpr$^{+/-}$ mice to generate FcγRIIB deficient lpr/B6 mouse (FcγRIIB$^{-/-}$/lpr$^{+/+}$=FcγRIIB$^{-/-}$/lpr). The above-mentioned FcγRIIB deficient B6 mice are short-lived compared to wild-type mice, wherein notable lymphocytes proliferation is observed, and anti-DNA antibody titer is significantly high. Moreover, glomerulonephritis is developed spontaneously 100% by 16-week-old, and arthritis is developed spontaneously 100% by 24-week-old, thus the present inventors found that by introducing FcγRIIB deficient gene into Lpr/B6 mouse, the mouse develops severe systemic lupus erythematosus. Thus the present invention has been completed.

DISCLOSURE OF THE INVENTION

The present invention relates to: a non-human animal model of systemic lupus erythematosus wherein a gene inducing lymphoproliferation is introduced into a non-human animal that does not develop spontaneously autoimmune pathology although its autoantibody response is enhanced ("1"); the non-human animal model of systemic lupus erythematosus according to "1", wherein the introduction method of a gene inducing lymphoproliferation is to intercross a non-human animal that does not develop spontaneously autoimmune pathology although its autoantibody response is enhanced, with a non-human animal expressing a gene inducing lymphoproliferation, and to intercross thus obtained heterozygous mice ("2"); the non-human animal model of systemic lupus erythematosus according to "1" or "2", wherein the non-human animal that does not develop spontaneously autoimmune pathology although its autoantibody response is enhanced is a non-human animal whose FcγRIIB gene function is deficient on its chromosome ("3"); the non-human animal model of systemic lupus erythematosus according to any one of "1" to "3" wherein the gene inducing lymphoproliferation is Lpr gene "4"; the non-human animal model of systemic lupus erythematosus according to any one of "1" to "4", wherein the non-human animal is a mouse ("5"); the non-human animal model of systemic lupus erythematosus according to "5", wherein the mouse whose FcγRIIB gene function is deficient on its chromosome is a C57BL/6J(B6) mouse whose FcγRIIB gene function is deficient on its chromosome ("6"); the non-human animal model of systemic lupus erythematosus according to "5", wherein the mouse expressing the gene inducing lymphoproliferation is an lpr/C57Bl/6J(B6) mouse ("7").

The present invention further relates to: a screening method for a therapeutic agent for systemic lupus erythematosus wherein a test substance is administered to the non-human animal model of systemic lupus erythematosus according to any one of "1" to "7", and the change in average life expectancy, the change in tissues, organs or cells, and/or change in antinuclear antibody titer in sera are measured and evaluated ("8"); a screening method for a therapeutic agent for systemic lupus erythematosus wherein a tissue, an organ or cells derived from the non-human animal model of systemic lupus erythematosus according to any one of "1" to "7" is contacted with a test substance, and the change in tissues, organs or cells is measured and evaluated ("9"); the screening method for a therapeutic agent for systemic lupus erythematosus according to "8" or "9", wherein the change in tissues or organs is a change in kidney or foot joint ("10"); the screening method for a therapeutic agent for systemic lupus erythematosus according to "8" or "9", wherein the change in cells is a change in proliferation or decrease of B cells, or a change in differentiation of B cells ("11"); the screening method for a therapeutic agent for systemic lupus erythematosus according to "11", wherein the B cells are derived from abdominal cells or splenic cells ("12"); the screening method for a therapeutic agent for systemic lupus erythematosus according to "8", wherein the change in antinuclear antibody titer in sera is a change in anti-double stranded antibody titer and/or anti-single stranded DNA antibody titer in sera ("13"); the screening method for a therapeutic agent for systemic lupus erythematosus according to any one of "8" to "13", wherein the case of the non-human animal model of systemic lupus erythematosus according to any one of "1" to "7" is compared with the case of a wild-type non-human animal and evaluated ("14"); a therapeutic agent for systemic lupus erythematosus which can be obtained by the screening method for a therapeutic agent for systemic lupus erythematosus according to any one of "8" to "14" ("15").

BEST MODE OF CARRYING OUT THE INVENTION

Figure 1:
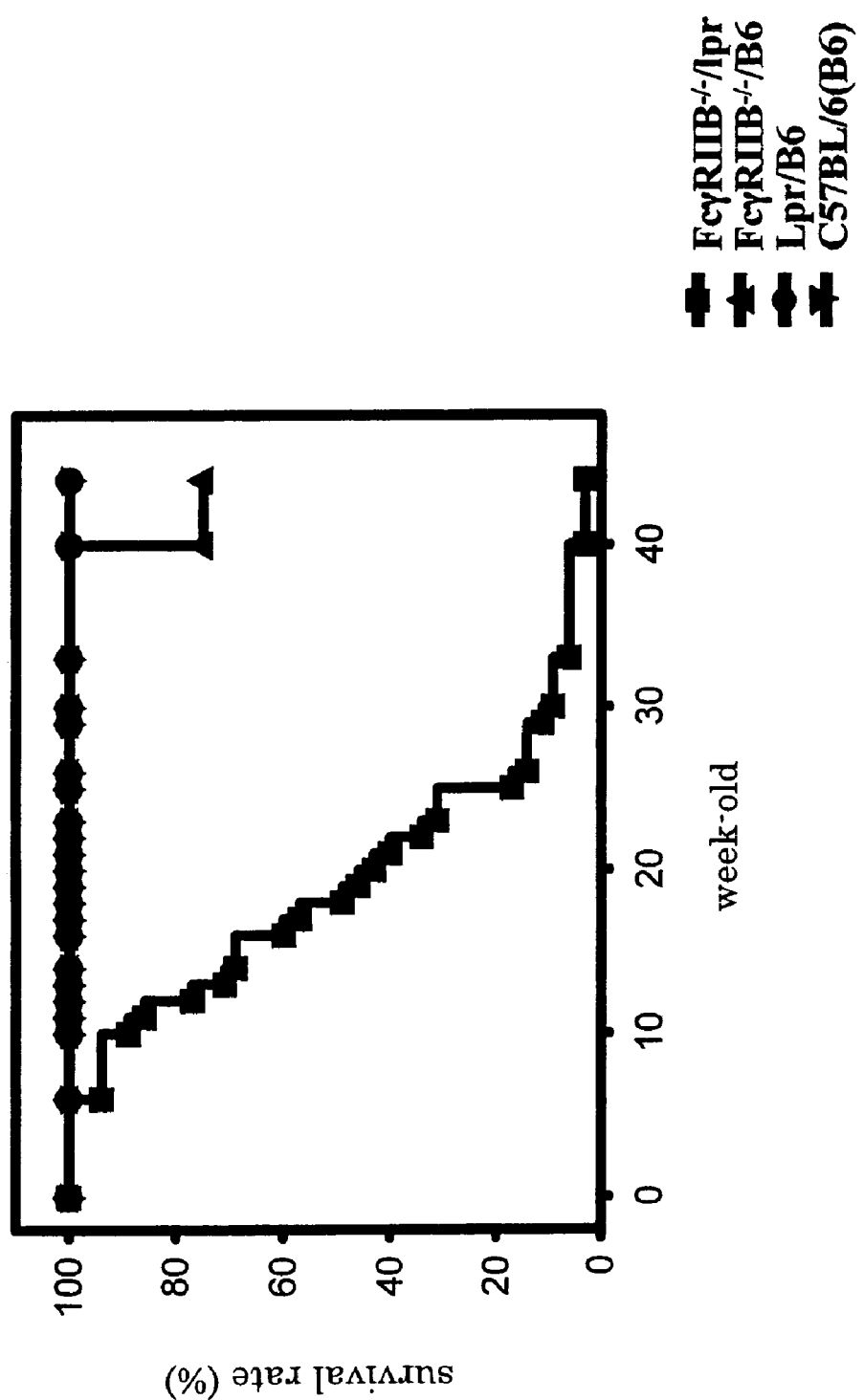
FIG. 1 shows the survival rate curve of FcγRIIB deficient lpr/B6 mouse, Lpr/B6 mouse, FcγRIIB deficient B6 mouse, and C57BL/6J mouse of the present invention.

As for the non-human animal model of systemic lupus erythematosus of the present invention, there is no specific limitation as long as it is a non-human animal wherein generation of antinuclear antibody such as anti-double stranded DNA antibody, anti-single stranded DNA antibody and the like is induced and arthritis and glomerulonephritis are developed spontaneously by introducing a gene inducing lymphoproliferation such as Lpr gene and the like, into a non-human animal that does not develop spontaneously autoimmune pathology although its autoantibody response is enhanced. As for the above-mentioned method for introducing a gene inducing lymphoproliferation such as Lpr gene and the like, it can be particularly exemplified by known methods for introducing a gene using a promoter, virus and the like, but it is not limited to these. It can be also exemplified by the method wherein a non-human animal expressing a gene inducing lymphoproliferation is intercrossed with a non-human animal that does not develop spontaneously autoimmune pathology although its autoantibody response is enhanced, and thus obtained heterozygous non-human animals are further crossed, and a gene inducing lymphoproliferation is introduced into the offsprings of a non-human animal that does not develop spontaneously autoimmune pathology although its autoantibody response is enhanced and a non-human animal expressing a gene inducing lymphoproliferation.

As for the above-mentioned non-human animal that does not develop spontaneously autoimmune pathology although its autoantibody response is enhanced, there is no specific limitation as long as it does not develop spontaneously autoimmune pathology such as glomerulonephritis, mucocutaneous symptoms, arthritis, pleurisy/pericarditis, neuropsychiatric symptoms and the like, although various autoantibody responses are enhanced. For example, it can be particularly exemplified by a non-human animal and the like whose FcγRIIB gene function is deficient on its chromosome. The non-human animal whose FcγRIIB gene function is deficient on its chromosome relates to a non-human animal which has lost the function to express FcγRIIB as a result of whole or a part of endogenous gene encoding FcγRIIB of the non-human animal is inactivated due to the gene mutation such as destruction, deficiency, substitution and the like. As for the non-human animal of the present invention, rodents such as mouse, rat and the like can be concretely exemplified, but it is not limited to these.

The wild-type non-human animal of the present invention relates to an animal of the same species as the above-mentioned non-human animal of systemic lupus erythematosus, and it can be preferably exemplified by its littermate. It is preferable to use simultaneously the non-human animal model of systemic lupus erythematosus and its littermate wild-type animal that are born according to Mendel's law, as it is possible to perform accurate comparative experiments at an individual level. The non-human animal model of systemic lupus erythematosus of the present invention can be preferably exemplified by a mouse whose FcγRIIB gene function is deficient on its chromosome and which expresses Lpr gene (FcγRIIB$^{-/-}$/lpr mouse), and the wild-type non-human animal can be preferably exemplified by a wild-type littermate mouse of the FcγRIIB$^{-/-}$/lpr mouse, respectively. It will be explained by taking as an example the case where the non-human animal is a mouse.

As for the method for generating a mouse whose FcγRIIB gene function is deficient on its chromosome and which expresses Lpr gene i.e. FcγRIIB$^{-/-}$/lpr mouse, there is no limitation as long as it is a method which can generate a mouse that develops systemic lupus erythematosus and particularly severe systemic lupus erythematosus. However, it can be particularly exemplified by a method wherein a FcγRIIB deficient B6 male mouse, which is inbred by backcrossing a mouse whose FcγRIIB gene function is deficient on its chromosome into a C57BL/6J(B6) mouse which is a haplotype H-2b, is intercrossed with Lpr/C57BL/6J(B6) female mouse expressing Lpr gene which is a gene inducing lymphoproliferation, to generate FcγRIIB$^{+/-}$/lpr$^{+/-}$ mouse wherein both genes are heterozygous, and the FcγRIIB$^{+/-}$/lpr$^{+/-}$ mice were further intercrossed each other to generate FcγRIIB$^{-/-}$/lpr mice (FcγRIIB deficient lpr/B6).

Besides, the above-mentioned mouse whose FcγRIIB gene function is deficient on its chromosome, namely a FcγRIIB knockout mouse, can be generated according to the method previously described by the present inventors (Nature 379, 346-349, 1996) and the like. In concrete terms, FcγRIIB gene is screened using a gene fragment obtained from the mouse gene library by a method such as PCR method or the like, and the screened FcγRIIB gene is subcloned using a virus vector and the like, and determined by DNA sequencing. A target vector is prepared by substituting the fragment containing $S_2$ exon and $EC_1$ exon of the clone to a pMC1 neo gene cassette and the like. The linearized vector is introduced into ES cells by electroporation and the like to cause homologous recombination. Among the homologous recombinants, ES cells showing resistance to G418 and the like are selected, and the clones of those cells are microinjected into a murine blastocyst, and the blastocyt is placed back to the host parent to generate a chimeric mouse. When this chimeric mouse is intercrossed with a wild-type mouse, heterozygous mouse can be obtained, and by intercrossing the heterozygous mice, FcγRIIB knockout mouse can be obtained.

The non-human animal model of systemic lupus erythematosus of the present invention is useful for the analysis of development mechanism of systemic lupus erythematosus, and by using the non-human animal model of systemic lupus erythematosus, a therapeutic method such as a therapeutic agent for systemic lupus erythematosus can be developed.

As for the screening method for a therapeutic agent for systemic lupus erythematosus of the present invention, it can be particularly exemplified by a method wherein a test substance is administered to a non-human animal model of systemic lupus erythematosus of the present invention, change in average life expectancy, change in tissues, organs or cells, and/or change in antinuclear antibody titer in sera are measured and evaluated, and a substance in which the change in average life expectancy, the change in tissues, organs or cells, and/or the change in antinuclear antibody titer in sera and the like are improved is determined. However, it is not limited to these methods. As for the above-mentioned method for measuring and evaluating the change in average life expectancy, it can be exemplified by a method wherein the change in average life expectancy is measured and evaluated in the cases wherein a test substance is used and wherein it is not used, to determine a substance with prolonged life expectancy. As for the method for measuring and evaluating the change in tissues or organs, it can be exemplified by a method wherein the change in tissues or organs of kidney, foot joint and the like is measured and evaluated in the cases wherein a test substance is used and wherein it is not used, to determine a substance in which tissues or organs are improved. As for the method for measuring and evaluating the change in cells, it can be exemplified by a method wherein the change in proliferation or decrease of B cells derived from abdominal cells or splenic cells, and the change in differentiation of B cells derived from abdominal cells or splenic cells are measured and evaluated in the cases wherein a test substance is used and wherein it is not used, to determine a substance in which dysfunction of the cells is improved. As for the method for measuring and evaluating the change in antinuclear antibody titer in sera, it can be exemplified by a method for measuring and evaluating the increase or decrease of antinuclear antibody titer in sera such as anti-single stranded DNA antibody titer anti-double stranded DNA antibody titer and the like in the cases wherein a test substance is used and wherein it is not used, to determine a substance in which antinuclear antibody titer is decreased in sera.

As for the screening method for a therapeutic agent for systemic lupus erythematosus of the present invention can be particularly exemplified a method wherein tissues, organs or cells derived from a non-human animal model of systemic lupus erythematosus of the present invention is contacted with a test substance, and the change in tissues, organs or cells is measured and evaluated to determine a substance in which tissues, organs, B cells and the like are improved. However it is not limited to these methods. The method for measuring and evaluating the change in tissues or organs can be exemplified by a method wherein the change in tissues or organs of kidney, foot joint and the like is measured and evaluated for the cases wherein a test substance is used and wherein it is not used, to determine a substance in which tissues or organs are improved. As for the method for measuring and evaluating the change in cells can be exemplified by a method wherein the change in proliferation or decrease of B cells derived from abdominal cells or splenic cells, and the change in differentiation of B cells derived from abdominal cells or splenic cells are measured and evaluated in the cases wherein a test substance is used and wherein it is not used, to determine a substance in which dysfunction of the cells is improved. The methods for measuring and evaluating are not particularly limited to these examples, however, it is more preferable to compare a non-human animal model of systemic lupus erythematosus with its littermate wild-type non-human animal and evaluate, when screening of a therapeutic agent for systemic lupus erythematosus in view of confirming whether there is a side effect or not.

The therapeutic agent for systemic lupus erythematosus that develops glomerulonephritis, arthritis, vasculitis, and cryoglobulinemia, which can be obtained by the screening method for a therapeutic agent for systemic lupus erythematosus of the present invention, can be used for therapy and the like for patients who have developed systemic lupus erythematosus. The therapeutic agent for systemic lupus erythematosus of the present invention can be administered orally or parenterally. As for the formulation for oral administration, it can be in the form of solid agent such as powder medicine, granules, capsules, tablets and the like, or liquid agent such as syrup, elixir and the like. As for the formulation for parenteral administration, it can be in the form of injectable solution, percutaneous agent, suppository and the like. These formulations can be produced according to a conventional method by adding auxiliaries being pharmacologically and pharmaceutically acceptable to an active ingredient. As for the auxiliary, pharmaceutical ingredients including the following: excipient such as soft silicic acid anhydride, starch, lactose, crystalline-cellulose, lactose calcium and the like; disintegrant such as carboxymethylcellulose and the like; lubricant such as magnesium stearate are used for oral form and formulation for mucous administration; pharmaceutical ingredients including the following: solvent or solubilizing agent such as physiological saline, mannitol, propylene glycol and the like; suspending agent such as detergent and the like are used for injectable solution, and pharmaceutical ingredients including aqueous or oleaginous solvent or solubilizing agent, adhesive and the like are further used for external preparation. Further, the dosage can be decided according to the type of targeted diseases, the age, sex, body-weight, and symptoms of patients, and administration form.

The present invention will be described in detail with reference to the following examples, while the technical scope of the present invention will not be limited to these examples.

REFERENCE EXAMPLE

Generation of FcγRIIB Deficient Mice

A clone of genomic DNA of FcγRIIB gene was isolated by screening the genomic DNA library of 129/Sv/J (H-2b) mouse. A 2.65 Kb fragment containing two independent exons i.e. $S_2$ and $EC_1$ of the clone was substituted by a pMC1 neo gene cassette (Toyobo) to construct a target vector. The linearized vector was introduced into ES cells (J1) by electroporation and to cause homologous recombination.

ES clones were isolated from the above-mentioned ES cells wherein homologous recombination has occurred, neomycin resistant ES clones were screened for G418 and GANC (gancyclovir), and a homologous recombinant was identified by Southern Blot Analysis. Genomic DNA was isolated from the homologous recombinant and digested with HindIII. Then it was verified that targeted allele containing pMC1 neo gene cassette was included. The verified ES clones were microinjected into a blastcyst to generate a chimeric mouse, and the generated chimeric mouse was intercrossed with a wild-type C57BL/6(H-2b) mouse to obtain a heterozygous mouse. Further, in order to obtain a homozygous mouse the heterozygous mice were intercrossed to generate a deficient mouse whose FcγRIIB gene is deficient on its chromosome.

EXAMPLE 1

Generation of FcγRIIB Deficient lpr/B6 Mice

The above-mentioned FcγRIIB deficient mouse was backcrossed into a C57BL/6J mouse (B6) which is a haplotype H-2b for 12 generations to generate an FcγRIIB deficient B6 mouse. The FcγRIIB deficient B6 male mouse was intercrossed with an Lpr/B6 female mouse to generate a FcγRIIB$^{+/-}$/lpr$^{+/-}$ mouse wherein both genes are heterozygous. The FcγRIIB$^{+/-}$/lpr$^{+/-}$ mice were further crossed each other to generate a FcγRIIB deficient lpr/B6 mouse. Discrimination of the FcγRIIB deficient lpr/B6 mouse was conducted by PCR method regarding Lpr and FcγRIIB deficiency. Lpr was discriminated by PCR method with the use of primers 5'-agcatagattccatttgct-3' (Seq. ID NO. 1; P1) and 5'-caaattttattgttgcgaca-3' (Seq. ID NO. 2; P2); wild-type (B6) was discriminated with primers 5'-agcatagattccatttgct-3' (Seq. ID NO. 3; P3) and 5'-agtaatgggctcagtgca-3' (Seq. ID NO. 4; P4). In the same manner, FcγRIIB deficiency was discriminated by PCR method with the use of 5'-ctcgtgctt-tacggtatcgcc-3' (Seq. ID NO. 5; P5) and 5'-ttgactgtggcct-taaacgtgtag-3' (Seq. ID NO. 6; P6); wild-type (B6) was discriminated with primers 5'-aaactcgacccccccgtggatc-3' (Seq. ID NO. 7; P7) and 5'-ttgactgtggccttaaacgtgtag-3' (Seq. ID NO. 8; P8).

EXAMPLE 2

Abnormality of FcγRIIB Deficient lpr/B6 Mice

In order to examine morphological abnormality of newborn FcγRIIB deficient lpr/B6 mice (FcγRIIB$^{-/-}$/lpr), they were compared with FcγRIIB deficient B6mice (FcγRIIB$^{-/-}$/B6), Lpr/B6 mice (Lpr/B6), or C57BL/6J mice (C57BL/6J (B6)), and their survival rates were examined (30 mice for each type). The results are shown in FIG. 1. Based on the results, it was verified that in FcγRIIB deficient lpr/B6 mice, deaths were observed at 6-week-old in the earliest case, then the survival rate was drastically lowered week by week. The average lifetime of the FcγRIIB deficient lpr/B6 mice was approximately 20-week-old, and their survival rate became approximately 0% at 40-week-old. Further, there was sex difference in the survival rate, and female mice died at earlier stage. On the contrary, no mouse died before 40-week-old in other three strains.

EXAMPLE 3

Figure 2:
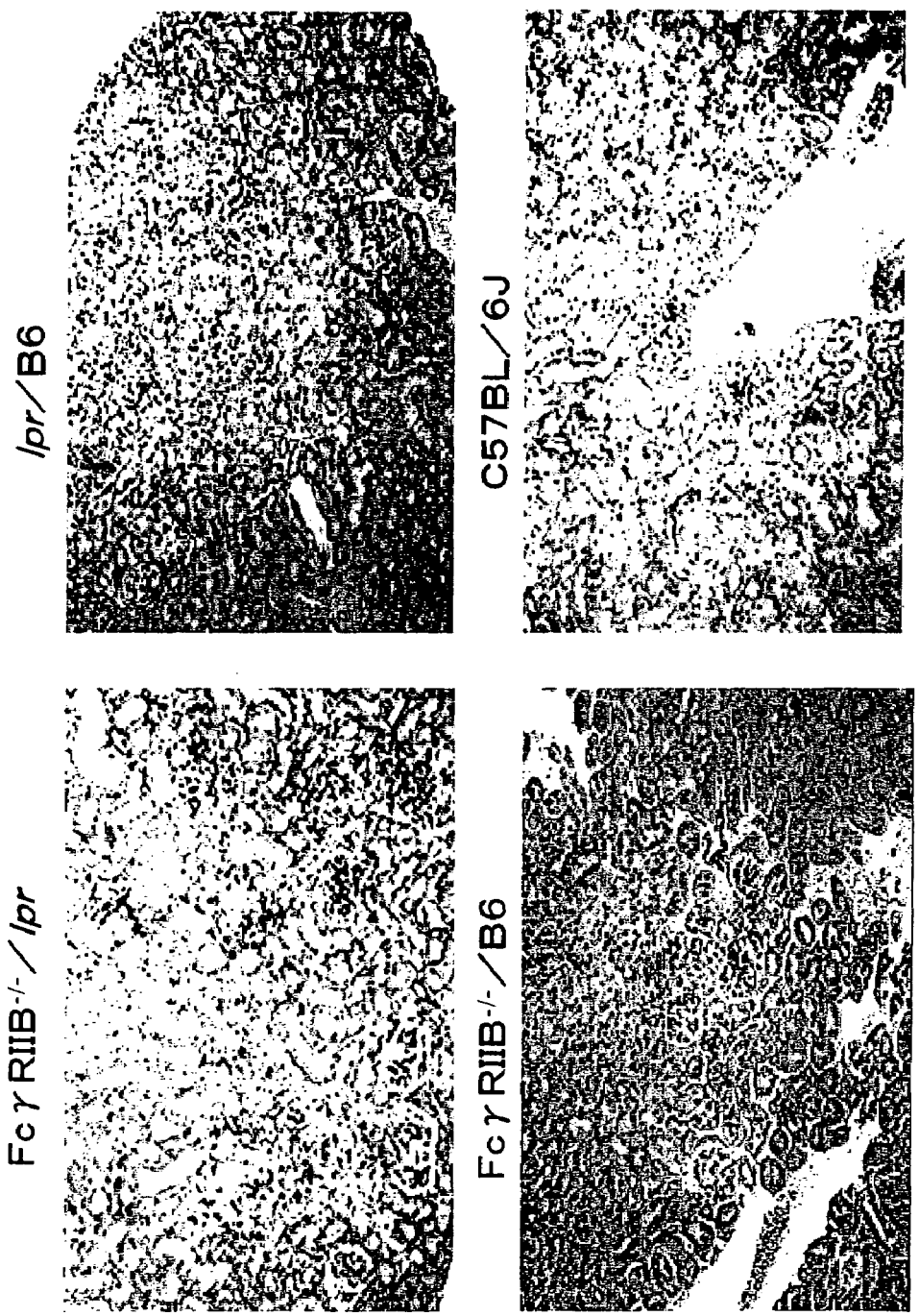
FIG. 2 is a set of photographs showing the observation results of the kidney specimens of FcγRIIB deficient lpr/B6 mouse, Lpr/B6 mouse, FcγRIIB deficient B6 mouse, and C57BL/6J mouse of the present invention (at 200-fold magnification).
Figure 3:
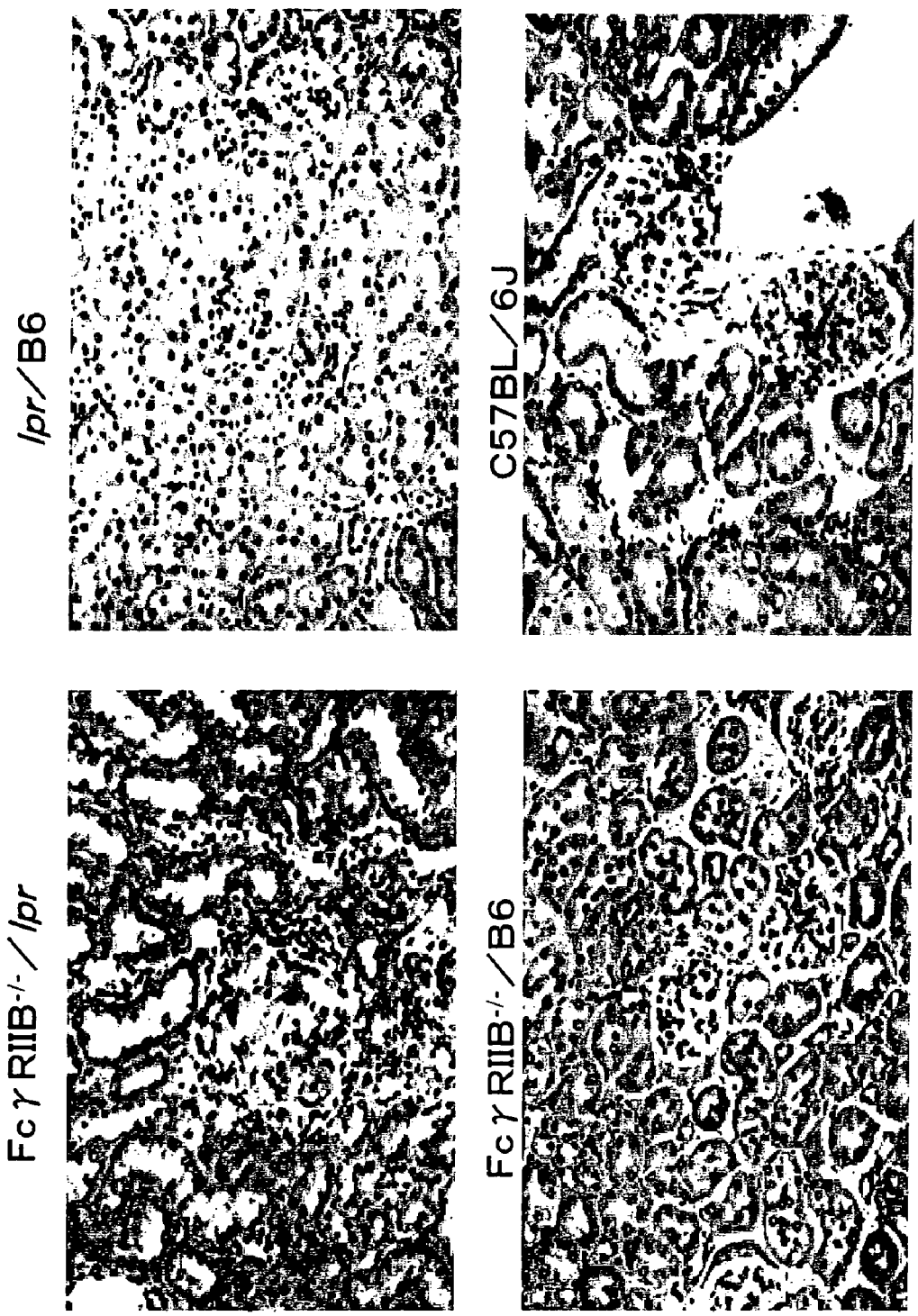
FIG. 3 is a set of photographs showing the observation results of the kidney specimens of FcγRIIB deficient lpr/B6 mouse, Lpr/B6 mouse, FcγRIIB deficient B6 mouse, and C57BL/6J mouse of the present invention (at 400-fold magnification).
Figure 4:
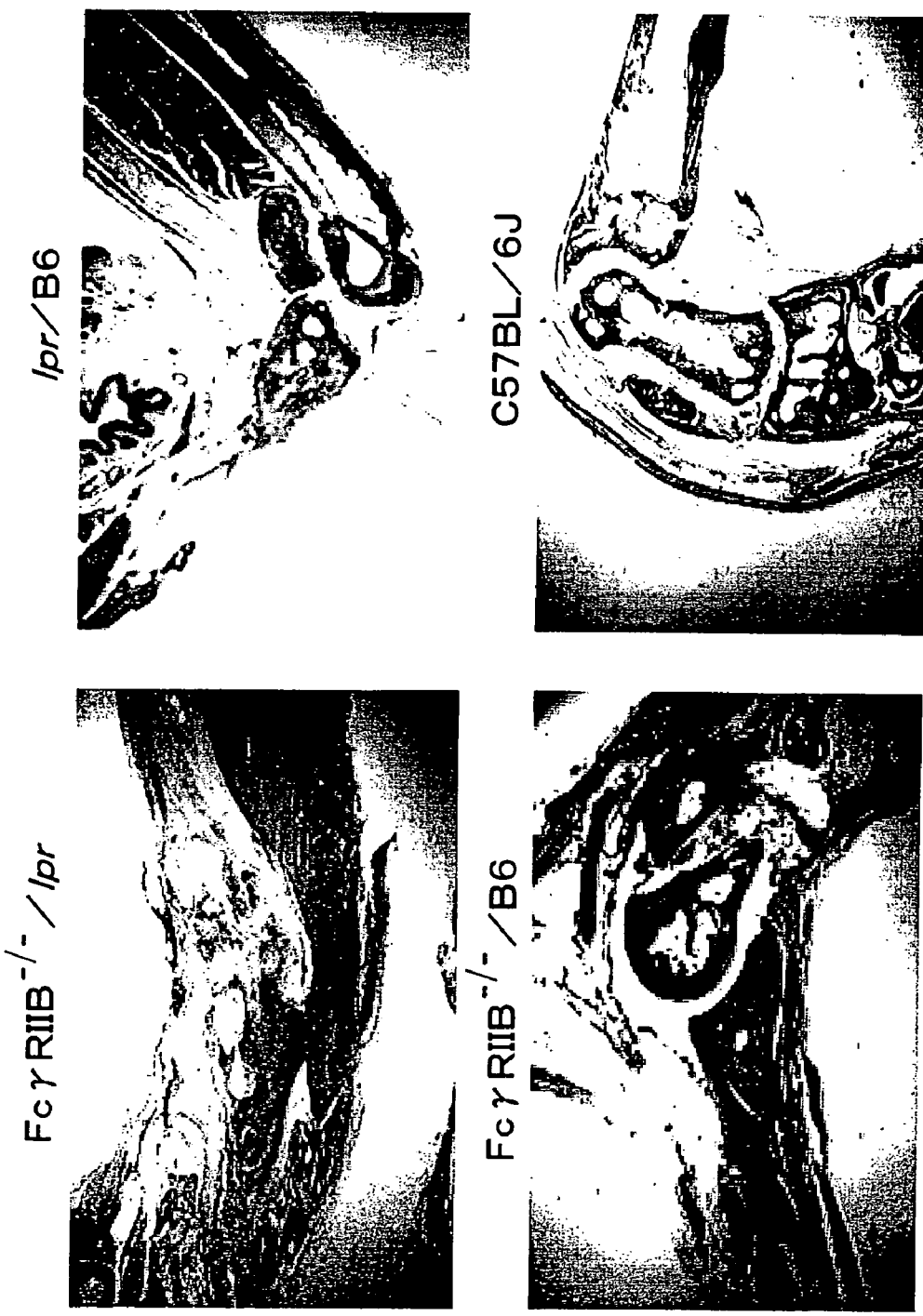
FIG. 4 is a set of photographs showing the observation results of the foot joint specimens of FcγRIIB deficient lpr/B6 mouse, Lpr/B6 mouse, FcγRIIB deficient B6 mouse, and C57BL/6J mouse of the present invention (at 40-fold magnification).
Figure 5:
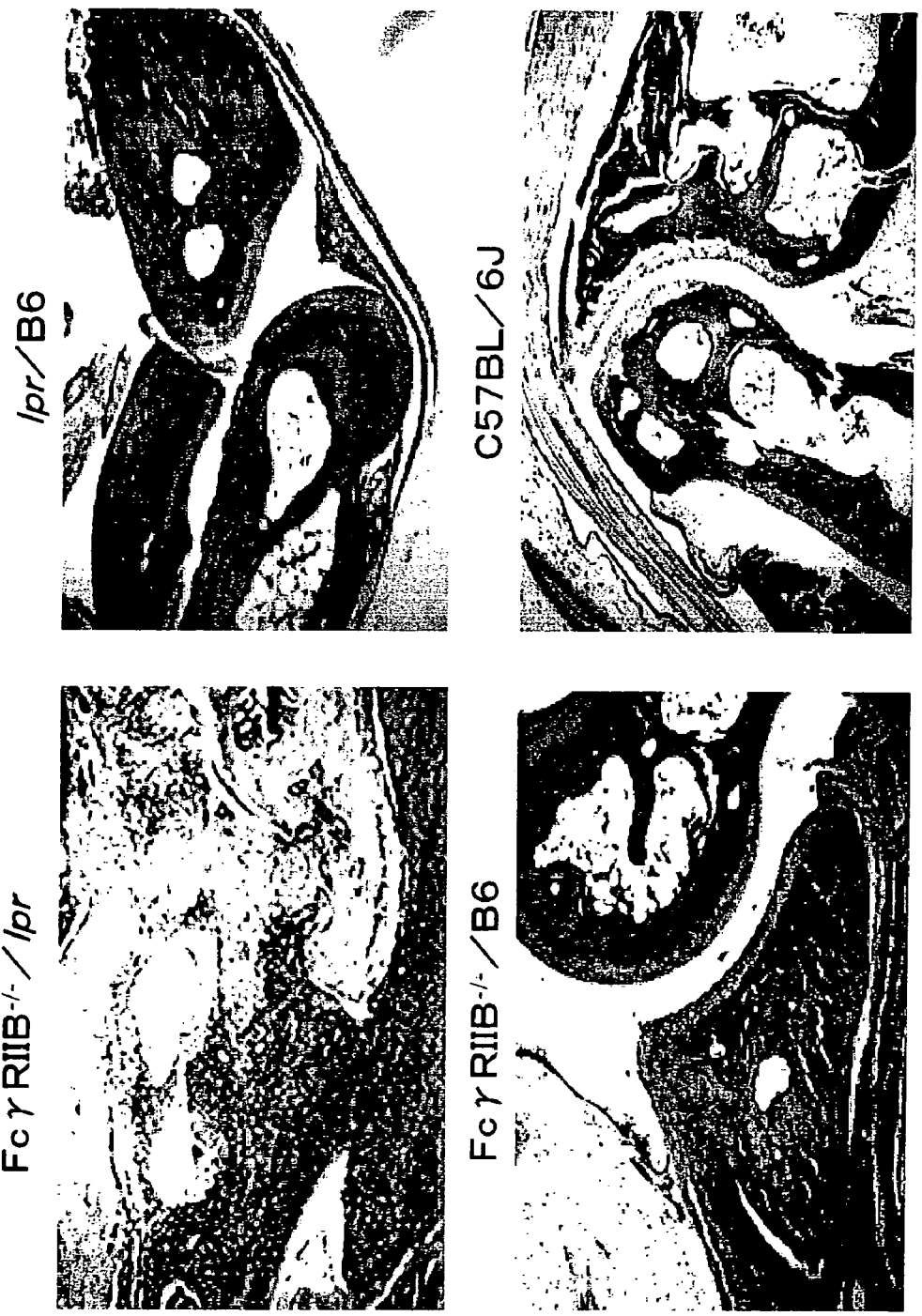
FIG. 5 is a set of photographs showing the observation results of the foot joint specimens of FcγRIIB deficient lpr/B6 mouse, Lpr/B6 mouse, FcγRIIB deficient B6 mouse, and C57BL/6J mouse of the present invention (at 100-fold magnification).

Spontaneous Development of Glomerulonephritis and Arthritis in FcγRIIB Deficient lpr/B6 Mouse Next, for the purpose of histopathological investigation of FcγRIIB deficient lpr/B6 mouse, FcγRIIB deficient lpr/B6 mice (FcγRIIB$^{-/-}$/lpr), FcγRIIB deficient B6 mice (FcγRIIB$^{-/-}$/B6), Lpr/B6 mice (Lpr/B6), and C57BL/6J mice (C57BL/6J) which were generated according to the method described in Example 1 were etherized and killed, and their specimen of kidney (FIGS. 2 and 3) and foot joint (FIGS. 4 and 5) were stained with hematoxylin and eosin, and visualized, respectively. The results are shown in FIG. 2 to 5, respectively. Meanwhile, FIG. 2 shows the kidney specimen of each 24-week-old mouse visualized at 200-fold magnification, FIG. 3 shows the kidney specimen of 24-week-old each mouse visualized at 400-fold magnification, FIG. 4 shows the foot joint specimen of 24-week-old each mouse visualized at 40-fold magnification, and FIG. 5 shows the foot joint specimen of 24-week-old each mouse visualized at 100-fold magnification. These results show that spontaneous development of glomerulonephritis and arthritis was verified in FcγRIIB deficient lpr/B6 mice from the age of 8-week-old. In kidney, glomerulonephritis with formation of a crescentic (FIGS. 2 and 3) was observed in 100% of FcγRIIB deficient lpr/B6 mice by 16-week-old, and in foot joint, arthritis with infiltration of neutrophil and lymphocyte (FIGS. 4 and 5) was observed in 100% of FcγRIIB deficient lpr/B6 mice by 24-week-old. However, any observation of destructivity in foot joint was seen.

EXAMPLE 4

Proliferation of B1 Cells and Plasma Cells in FcγRIIB Deficient lpr/B6 Mouse

Figure 6:
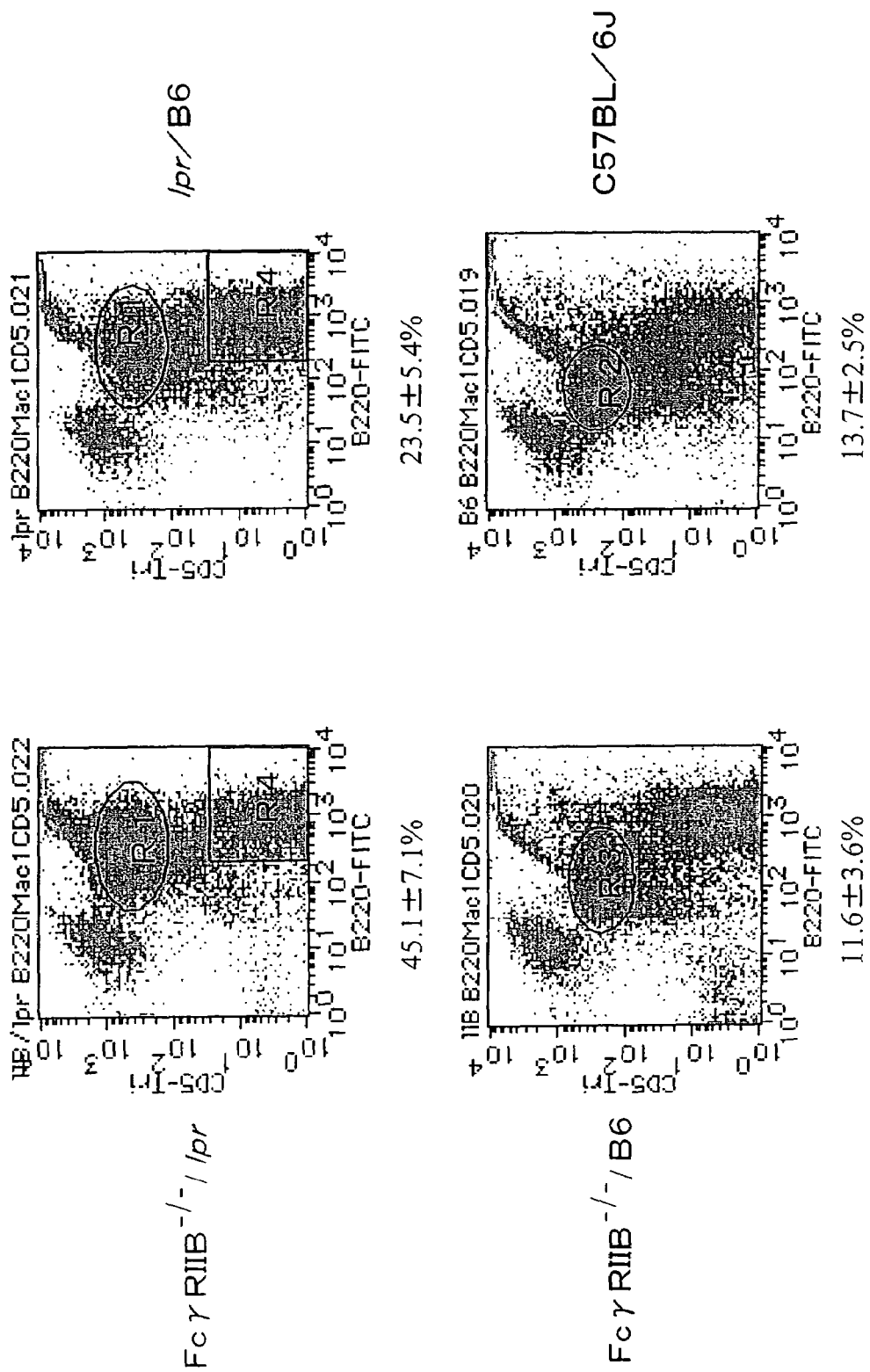
FIG. 6 is a set of drawings showing the FACS image wherein abdominal cells of 24-week-old mice from 4 strains (FcγRIIB deficient lpr/B6 mouse, Lpr/B6 mouse, FcγRIIB deficient B6 mouse, and C57BL/6J mouse) are evolved with B220 (horizontal axis) and CD5 (longitudinal axis).

Since diffuse glomerulonephritis and arthritis with inflammatory cell infiltration were observed in the above-mentioned FcγRIIB deficient lpr/B6 mice, proliferative response of B cells and differentiation of B cells in FcγRIIB deficient lpr/B6 mice were examined. Abdominal cells were isolated respectively from 24-week-old FcγRIIB deficient lpr/B6 mice (FcγRIIB$^{-/-}$/lpr); FcγRIIB deficient B6 mice (FcγRIIB$^{-/-}$/B6), Lpr/B6 mice (Lpr/B6), and C57BL/6J mice (C57BL/6J) of, and the abdominal cells were stained with anti-mouse CD5 antibody to which TRI color is bound (Ly-1)(CD5-Tri), and anti-mouse B220 antibody to which FITC is bound (RA3-6B2)(B220-FITC) according to a known method, and analyzed by flow cytometry. The results are shown in FIG. 6. These results show that B1 cells are significantly increased (B220$^+$CD5$^+$ cells; elliptic part) in FcγRIIB deficient lpr/B6 mice, and the B1 cell count is in the order of FcγRIIB$^{-/-}$/lpr>lpr/B6>FcγRIIB$^{-/-}$/B6=C57BL/6J.

Figure 7:
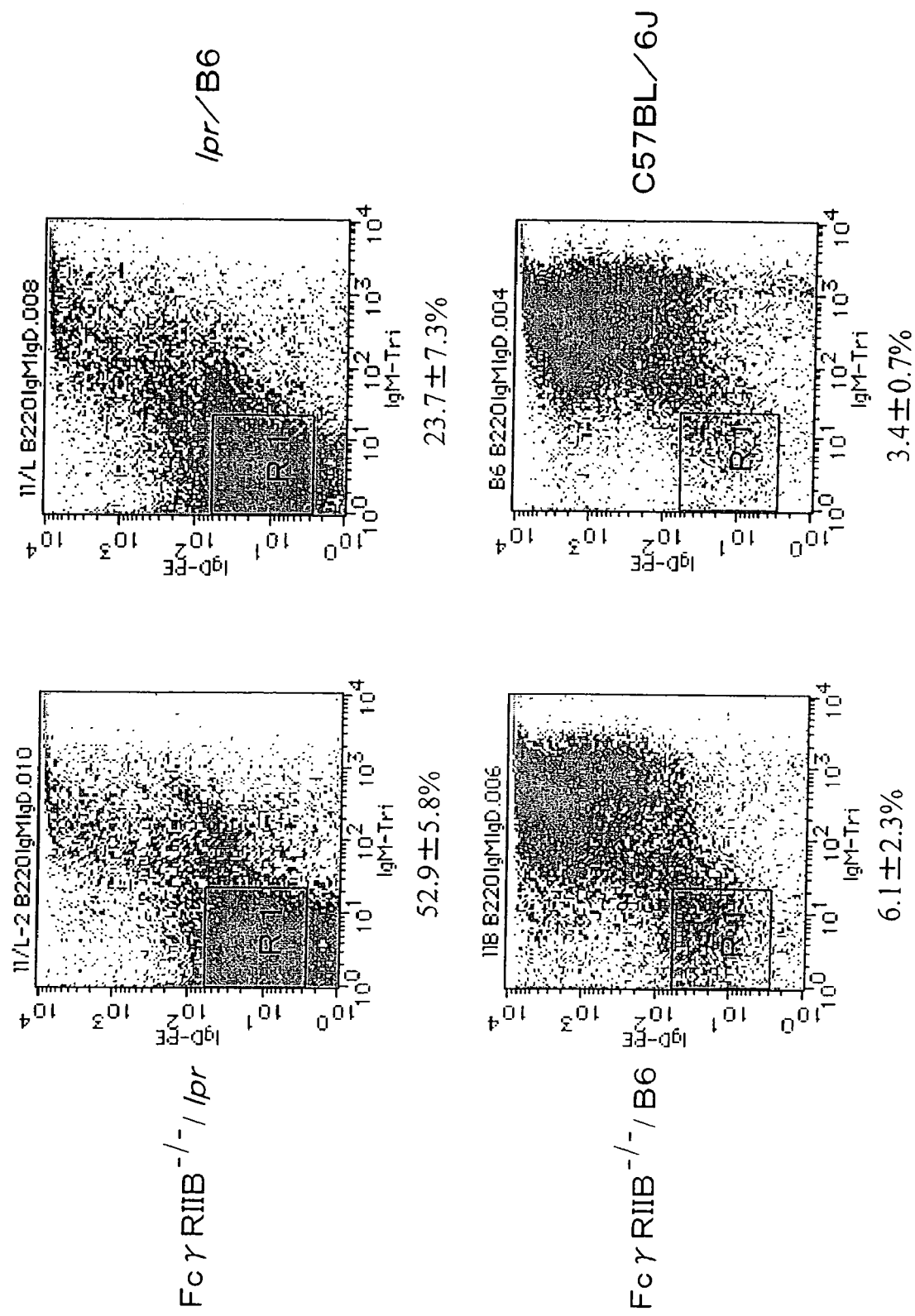
FIG. 7 is a set of drawings showing the FACS image wherein B220+ cells of splenic cells of 24-week-old mice from 4 strains (FcγRIIB deficient lpr/B6 mouse, Lpr/B6 mouse, FcγRIIB deficient B6 mouse, and C57BL/6J mouse) are evolved with IgM (horizontal axis) and IgD (longitudinal axis).

Next, splenic cells were isolated from FcγRIIB deficient lpr/B6 mice (FcγRIIB$^{-/-}$/lpr), FcγRIIB deficient B6 mice (FcγRIIB–/–/B6), Lpr/B6 mice (Lpr/B6), and C57BL/6J mice (C57BL/6J) respectively, and B220+cells were selected from the splenic cells by MACS sorting wherein B220-beads (Miltenyl Biotec) were used. The B220$^+$ cells were stained using monoclonal antibodies such as anti-mouse IgD antibody to which PE (phycoerythrin) is bound (11-26) (IgD-PE), anti-mouse IgM antibody to which Tri color is bound (R6-60.2) (IgM-Tri) and the like (all antibodies were from BD PharMingen) according to a known method, and differentiation of B cells was examined by flow cytometry analysis. The results are shown in FIG. 7. The results show that plasma cells are significantly increased (B220$^+$IgM$^-$/IgD$^-$ cells; square part) in FcγRIIB deficient lpr/B6 mice, and the plasma cell count is in the order of FcγRIIB$^{-/-}$/lpr>Lpr/B6>FcγRIIB$^{-/-}$/B6=C57BL/6J.

EXAMPLE 5

Development of Systemic Lupus Erythematosus in FcγRIIB Deficient lpr/B6 Mice

Figure 8:
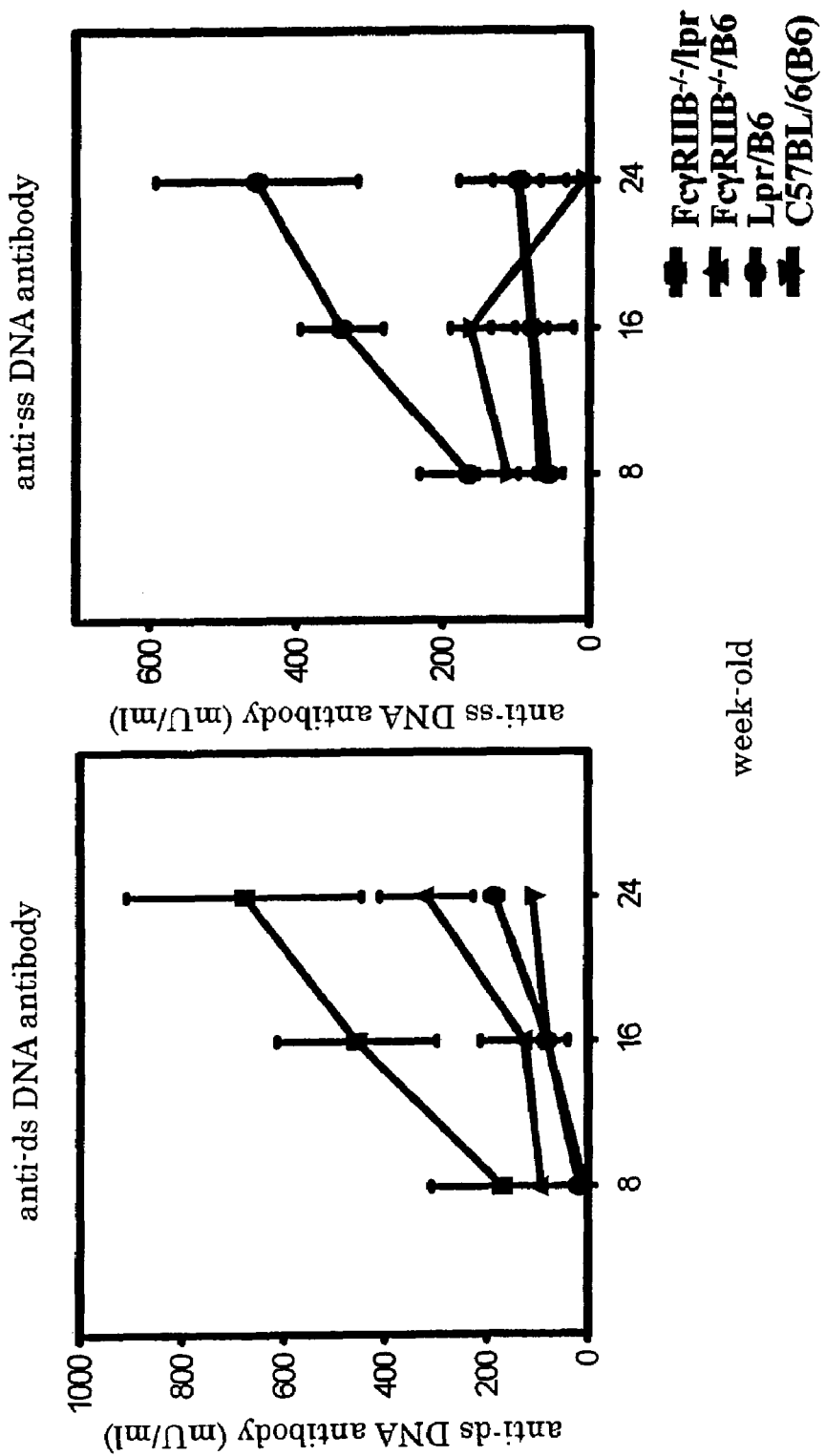
FIG. 8 is a set of drawings showing the results of examining anti-double stranded DNA antibody titer and anti-single DNA antibody titer of FcγRIIB deficient lpr/B6 mouse, Lpr/B6 mouse, FcγRIIB deficient B6 mouse, and C57BL/6J mouse.

As for the cause of systemic lupus erythematosus, dysfunction of T cells and B cells that induces generation of autoantibodies such as anti-double stranded DNA antibody (anti-ds DNA antibody), anti-single stranded DNA antibody (anti-ss DNA antibody) and the like is known (Theofilopoulos, A. N., and F. J. Dixon: Murine models of systemic lupus erythematosus. Adv. Inimunol. 37: 269-390, 1985). Therefore, in order to examine whether systemic lupus erythematosus is developed in FcγRIIB deficient lpr/B6 mice, anti-double stranded DNA antibody titer and anti-single stranded DNA antibody titer in FcγRIIB deficient lpr/B6 mice were examined. Sera were collected from the eye sockets of FcγRIIB deficient lpr/B6 mice (FcγRII$^{-/-}$/lpr), FcγRIIB deficient B6 mice (FcγRIIB$^{-/-B}$6), Lpr/B6 mice (Lpr/B6), and C57BL/6J mice (C57BL/6J (B6)) at the age of 8-, 16-, 24-week-old, detected with anti-ds or ss-DNA mouse ELISA kit (Shibayagi), and each antibody titer was measured using Biolumin 960 Microplate Reader (Molecular Dynamics) with an absorbance of 450 nm. The results are shown in FIG. 8. Based on the results, it was verified that anti-ds DNA antibody titer and ss-DNA antibody titer as autoantibodies were significantly increased at the age of 16- and 24-week-old, compared to other mice such as Lpr/B6 mice, FcγRIIB deficient B6 mice used for intercrossing, and further with their wild-type C57BL/6J (B6) mice. As a result of the above-mentioned, it was made clear that systemic lupus erythematosus is developed in FcγRIIB deficient lpr/B6 mice.

INDUSTRIAL APPLICABILITY

The non-human animal model of systemic lupus erythematosus of the present invention is useful in the study of development process of autoimmune diseases such as glomerulonephritis, arthritis, vasculitis, cryoglobulinemia and the like since it induces generation of anti-double stranded DNA antibody and anti-single stranded antibody, and it shows severe symptoms of systemic lupus erythematosus such as spontaneous sideration and the like of arthritis and glomerulonephritis. Further, it is possible to analyze the mechanism leading to systemic lupus erythematosus, and to study and develop a preventive and therapeutic method for the progression of systemic lupus erythematosus.

The invention claimed is:

1. A transgenic mouse that is FcγRIIB$^{-/-}$/lpr having a C57BL/6J background comprising a homozygous disruption of the FcγRIIB gene that results in no production of the FcγRIIB protein and further comprising a homozygous lpr mutation, wherein the mouse develops elevated anti-double stranded and anti-single stranded DNA antibodies, histopathological characteristics of diffuse glomerulonephritis, foot joint inflammation, and has reduced survival rates compared to, FcγRIIB$^{-/-}$/B6 mice, Lpr/B6 mice, or C57BL/6J mice.

* * * * *

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence

```
<220> FEATURE:
<223> OTHER INFORMATION: Description of Artificial Sequence: Synthetic
      PCR primer

<400> SEQUENCE: 1
agcatagatt ccatttgct                                                    19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 2
caaattttat tgttgcgaca                                                   20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 3
agcatagatt ccatttgct                                                    19

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 4
agtaatgggc tcagtgca                                                     18

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 5
ctcgtgcttt acggtatcgc c                                                 21

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 6
ttgactgtgg ccttaaacgt gtag                                              24

<210> SEQ ID NO 7
<211> LENGTH: 21
<212> TYPE: DNA
<213> ORGANISM: Artificial Sequence
<220> FEATURE:
```

-continued

```
<223> OTHER INFORMATION: Description of Artificial Sequence: Synthetic
      PCR primer

<400> SEQUENCE: 7
aaactcgacc ccccgtggat c                                              21

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 8
ttgactgtgg ccttaaacgt gtag                                           24
```